United States Patent
Kalindjian et al.

Patent Number: 5,912,260
Date of Patent: *Jun. 15, 1999

[54] GASTRIN AND CCK ANTAGONISTS

[75] Inventors: Sarkis Barret Kalindjian, Banstead; Nigel Paul Shankley, Pootings, Nr. Edenbridge; Robert Antony David Hull, Tonbridge; Atul Kotecha, London; Sonia Patricia Roberts, London; Elaine Anne Harper, London, all of United Kingdom

[73] Assignee: James Black Foundation Limited, Dulwich, United Kingdom

[*] Notice: This patent is subject to a terminal disclaimer.

[21] Appl. No.: 08/737,725

[22] PCT Filed: May 25, 1995

[86] PCT No.: PCT/GB95/01194

§ 371 Date: Dec. 19, 1996

§ 102(e) Date: Dec. 19, 1996

[87] PCT Pub. No.: WO95/32949

PCT Pub. Date: Dec. 7, 1995

[30] Foreign Application Priority Data

May 27, 1994 [GB] United Kingdom .................. 9410688
Aug. 9, 1994 [WO] WIPO .................. PCT/GB94/01741
Feb. 9, 1995 [GB] United Kingdom .................. 9502503

[51] Int. Cl.⁶ .................. A61K 31/40; A61K 31/415; A61K 31/41; C07D 235/06
[52] U.S. Cl. .................. 514/381; 548/250; 548/304.4; 548/510; 514/394; 514/415
[58] Field of Search .................. 548/304.4, 250, 548/510; 514/394, 381, 415

[56] References Cited

U.S. PATENT DOCUMENTS 5,387,600  2/1995  Aikawa et al. .................. 514/395

OTHER PUBLICATIONS

Tracey H.J. and Gregory R.A., Nature (London), 1964, vol. 204, pp. 935–938.

*Primary Examiner*—Laura L. Stockton
*Attorney, Agent, or Firm*—Foley & Lardner

[57] ABSTRACT

Described herein are compounds of formula (I) or a pharmaceutically acceptable salt thereof,

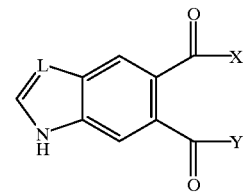

(I)

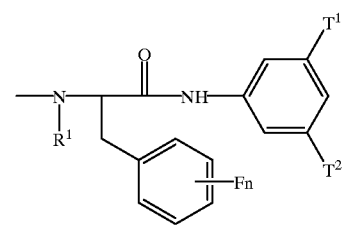

(II)

wherein L is N or C, one of X and Y is —NH—CH$_2$—R$^2$ and the other is the substituent of formula (II). The compounds are potent gastrin and/or CCK antagonists.

11 Claims, No Drawings

GASTRIN AND CCK ANTAGONISTS

This application is a 371 of PCT/GB95/01194 filed May 25, 1995.

This invention relates to gastrin and CCK antagonists. The invention also relates to methods for preparing such antagonists and to pharmaceutical compositions comprising such antagonists.

Gastrin and the CCK's are structurally-related neuropeptides which exist in gastrointestinal tissue and in the CNS (see Mutt V., *Gastrointestinal Hormones*, Glass G. B. J., ed., Raven Press, N.Y., p 169 and Nisson G., ibid, 127).

Gastrin is one of the three primary stimulants of gastric acid secretion. Several forms of gastrin are found including 34-, 17-, and 14-amino acid species with the minimum active fragment being the C-terminal tetrapeptide (TrpMetAspPhe-NH$_2$) which is reported in the literature to have full pharmacological activity (see Tracey H. J. and Gregory R. A., Nature (London), 1964, 204, 935). Much effort has been devoted to the synthesis of analogues of this tetrapeptide (and the N-protected derivative Boc-TrpMetAspPhe-NH$_2$) in an attempt to elucidate the relationship between structure and activity.

Natural cholecystokinin is a 33 amino acid peptide (CCK-33), the C-terminal 5 amino acids of which are identical to those of gastrin. Also found naturally is the C-terminal octapeptide (CCK-8) of CCK-33.

The cholecystokinins are reported to be important in the regulation of appetite. They stimulate intestinal motility, gall bladder contraction, pancreatic enzyme secretion, and are known to have a trophic action on the pancreas. They also inhibit gastric emptying and have various effects in the CNS.

Compounds which bind to gastrin and/or CCK receptors are important because of their potential pharmaceutical use as antagonists of the natural peptides.

A number of gastrin antagonists have been proposed for various therapeutic applications, including the prevention of gastrin-related disorders, gastrointestinal ulcers, Zollinger-Ellison syndrome, antral G cell hyperplasia and other conditions in which lowered gastrin activity is desirable. The hormone has also been shown to have a trophic action on cells and so an antagonist may be expected to be useful in the treatment of cancers, particularly in the stomach and the colon.

Possible therapeutic uses for cholecystokinin antagonists include the control of appetite disorders such as anorexia nervosa, and the treatment of pancreatic inflammation, biliary tract disease and various psychiatric disorders. Other possible uses are in the potentiation of opiate (e.g. morphine) analgesia, and in the treatment of cancers, especially of the pancreas. Moreover, ligands for cholecystokinin receptors in the brain (so-called CCK$_B$ receptors) have been claimed to possess anxiolytic activity.

The present invention provides compounds of the formula

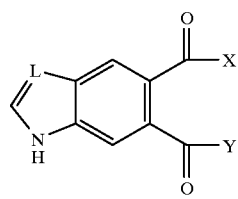

(I)

wherein

L is =N— or =CH—,
one of X and Y is —NH—CH$_2$—R$^2$ (wherein R$^2$ is cycloheptyl or 1-adamantyl) and the other is

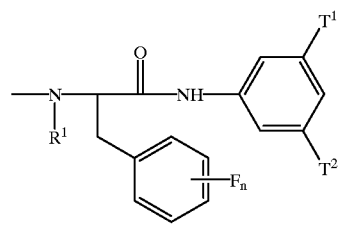

(II)

in which R$^1$ is H or methyl,

T$^1$ and T$^2$ are independently H or Z(CH$_2$)$_m$—, wherein m is from 0 to 3 and Z is a carboxy group, a tetrazolyl group, CF$_3$CONHSO$_2$—, PhCONHSO$_2$—, isopropyl-OC(O)NHSO$_2$— or a group selected from

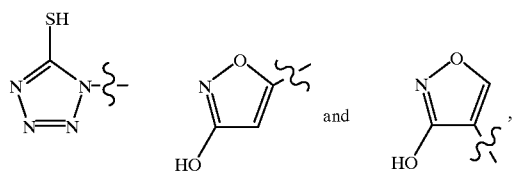

(provided that T$^1$ and T$^2$ are not both H and that T$^1$ and T$^2$ are not both carboxy when L is =CH—); and n is from 0 to 5

Such compounds have been found to act as gastrin and/or CCK antagonists in in vitro tests. Most importantly, they have been found to be active when administered orally.

The compounds of the invention exist in enantiomeric and tautomeric forms. It will be understood that the invention comprehends the different enantiomers and tautomers in isolation from each other, and also as mixtures.

The invention also comprehends derivative compounds ("pro-drugs") which are degraded in vivo to yield the species of formula (I). Pro-drugs are usually (but not always) of lower potency at the target receptor than the species to which they are degraded. Pro-drugs are particularly useful when the desired species has chemical or physical properties which make its administration difficult or inefficient. For example, the desired species may be only poorly soluble, it may be poorly transported across the mucosal epithelium, or it may have an undesirably short plasma half-life. Examples of pro-drug forms which may be used in the present invention are described in "Comprehensive Medicinal Chemistry", Volume 5 (ed. Taylor, J. B.), pages 122–132 (Pergamon, Oxford, 1990) and references contained therein.

The compounds of the invention may be prepared by reacting a compound of the formula

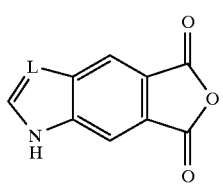

(III)

with a compound of the formula $H_2N$—$CH_2$—$R^2$ wherein L and $R^2$ are as defined above, and then reacting the product with a compound of the formula

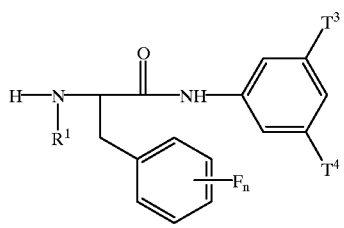
(IV)

wherein $R^1$ and n are as defined above, and $T^3$ and $T^4$ are independently H or Z' $(CH_2)_m$— (wherein m is from 0 to 3 and Z' is a protected carboxy group, a protected tetrazolyl group, $CF_3CONHSO_2$— or $PhCONHSO_2$—). Alternatively, the compound of formula (III) is first reacted with the compound of formula (IV) and the product is then reacted with the compound of formula $H_2N$—$CH_2$—$R^2$. In the case in which Z' is a protected group, the protecting group is then removed.

Suitable amidation methods are described in detail in "The Peptides, Vol. 1", Gross and Meinenhofer, Eds., Academic Press, N.Y., 1979. These include the carbodiimide method (using, for example, 1,3-dicyclohexylcarbodiimide [DCC] or 1-(3-dimethylaminopropyl)-3-ethylcarbodiimidehydrochloride [EDCI], and optionally an additive such as 1-hydroxybenzotriazole [HOBT] to prevent racemization), the azide method, the mixed anhydride method, the symmetrical anhydride method, the acid chloride method, the acid bromide method, the use of bis (2-oxo-3-oxazolidinyl) phosphinic chloride [BOP-Cl], the use of PyBOP or PyBrOP, the use of the isopropenylsuccinimido carbonate method and the active ester method (using, for example, N-hydroxysuccinimide esters, 4-nitrophenyl esters or 2,4,5-trichlorophenol esters).

The coupling reactions are generally conducted under an inert atmosphere, such as an atmosphere of nitrogen or argon. Suitable solvents for the reactants include methylene chloride, tetrahydrofuran [THF], dimethoxyethane [DME] and dimethylformamide [DMF].

The compounds of the invention in which Z is a group of the formula

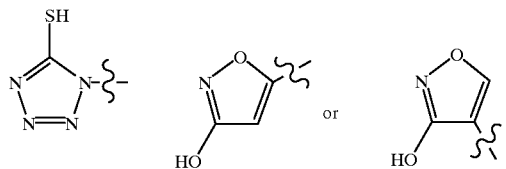
or may be prepared from suitable precursors such as the corresponding aniline or alcohol, which are then functionalised using standard methods.

Pharmaceutically acceptable salts of the acidic or basic compounds of the invention can of course be made by conventional procedures, such as by reacting the free base or acid with at least a stoichiometric amount of the desired salt-forming acid or base.

While the compounds of the invention can be administered orally, the present invention also comprehends administration by other routes including parenteral, intravenous, intramuscular, intraperitoneal, subcutaneous, rectal and topical (including transdermal) administration.

For oral administration, the compounds of the invention will generally be provided in the form of tablets or capsules or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

For topical administration, a wide variety of ointments or cream preparations can be used, or the drug in a suitable carrier may be delivered using a transdermal drug delivery system, such as a skin patch.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

Effective doses of the compounds of the present invention may be ascertained by conventional methods. The specific dosage level required for any particular patient will depend on a number of factors, including the route of administration, the severity of the condition being treated and the weight of the patient. In general, however, the daily dose (whether administered as a single dose or as divided doses) will be in the range 0.01 to 5000 mg per day, and more usually from 1 to 1000 mg per day. Expressed as dosage per unit body weight, a typical dose will be between 0.1 μg/kg and 50 mg/kg, and more usually between 1 μg/kg and 50 mg/kg. For oral administration a typical dose will be between 0.1 mg/kg and 20 mg/kg.

The invention is now further illustrated by means of the following examples.

EXAMPLE 1

5-(1S-(3,5-dicarboxyphenylaminocarbonyl)-2-(2-fluorophenyl)ethylaminocarbonyl)-6-(cycloheptanemethylaminocarbonyl)-benzimidazole a. Benzimidazole-5,6-dicarboxylic acid anhydride Benzimidazole-5,6-dicarboxylic acid (8.2 g), prepared from 5,6-dimethylbenzimidazole as described in J.Org.Chem. 1987, 52, 2934., was heated at 250° C. under vacuum (0.01 mm Hg) for 1 h. The solid was extracted with hot acetone and the acetone extracts were evaporated to give the title compound (6.1 g).

b. 5-(1S-(3,5-dibenzyloxycarbonylphenylaminocarbonyl)-2-(2-fluorophenyl)ethylaminocarbonyl)benzimidazole-6-carboxylic acid A solution containing the anhydride produced in step a (3.22 g, 17.1 mmol) and 1S-(3,5- dibenzyloxycarbonylphenylaminocarbonyl)-2-(2-fluorophenyl)ethylamine (9.00 g, 17.1 mmol), prepared as described below, in acetonitrile (170 ml) was heated under reflux for 1 h. The mixture was cooled and allowed to stand at 5° C. for 2 h. The resultant white crystals were filtered and dried to afford the title compound (10.87 g).

c. 5-(1S-(3,5-dibenzyloxycarbonylphenylaminocarbonyl)-2-(2-fluorophenyl)-ethylaminocarbonyl)-6-(cycloheptanemethylaminocarbonyl)benzimidazole A solution of the acid produced in step b (5.5 g, 7.89 mmol) and cycloheptanemethylamine (1.5 g, 11.86 mmol) in dry dimethylformamide (50 ml) was cooled to 0° C., 1-hydroxy-benzotriazole (1.07 g, 7.89 mmol) was added and the solution was stirred for 10 min. at this temperature. 1-(3-dimethylaminopropyl)-3-ethylcarbodiimide hydrochloride [EDCI] (1.51 g, 7.89 mmol) was added followed by 4-dimethylaminopyridine (catalytic quantity) and the stirring was continued for 1 h at 0° C. then overnight at room temperature. The solvent was evaporated under reduced pressure to approximately half the original volume and the residue was poured into water (500 ml). The resultant precipitate was filtered and dried and then purified by column chromatography (silica 5% methanol and 95% dichloromethane) yielding the title compound (4.95 g, 76%).

d. 5-(1S-(3,5-dicarboxyphenylaminocarbonyl)-2-(2-fluorophenyl)ethylaminocarbonyl)-6-(cycloheptanemethylaminocarbonyl)benzimidazole The product of step c (4.7 g, 5.7 mmol) was dissolved in a THF/methanol mixture (1:1 200 ml) and 10% palladium on-charcoal (500 mg) was added. The reaction mixture was stirred overnight under an atmosphere of hydrogen and then filtered through celite and evaporated to yield the title compound (3.5 g, 96%). $^1$H NMR (d$^6$-DMSO) δ13.0 (3H, br s), 10.2 (1H, br s), 8.9 (1H, d), 8.74 (2H, s), 8.7 (1H, t), 8.4 (1H, s), 8.2 (1H, s), 7.8 (1H, s), 7.5–7.1 (5H, m), 4.8 (1H, m), 3.5 (1H, m), 3.3–3.1 (3H, m), 1.6–1.1 (13H, m).

The compound was further characterised and tested as the di-N-methyl-D-glucamine salt. Found: C, 55.39; H, 6.85; N, 9.17. $C_{48}H_{68}FN_7O_{17}$ requires C, 55.75; H, 6.63; N, 9.48%

Preparation of 1S-(3,5-dibenzyloxycarbonylphenylaminocarbonyl)-2-phenylethylamine e. 3,5-dibenzyloxycarbonylnitrobenzene 5-nitro-isophthalic acid (21.1 g, 0.1 mol), thionyl chloride (80 ml) and DMF (10 drops) were stirred and heated for about 1 h until a clear solution was obtained. Excess thionyl chloride was removed by evaporation and the residual acid chloride was coevaporated with dichloromethane (2×100 ml) to remove the last traces.

Benzyl alcohol (21.6 g, 0.2 mol) and triethylamine (30.03 g, 0.3 mol) were dissolved in dichloromethane (200 ml) and stirred at 0° C. under an atmosphere of dry nitrogen and a solution of the acid chloride in dichloromethane (50 ml) was added dropwise over 20 min. The solution was stirred and refluxed for 1 h, and the solution was cooled. The organic layer was washed with water (2×100 ml), saturated sodium hydrogencarbonate solution (100 ml), and dried over magnesium sulphate. The solution was filtered and evaporated to leave the title compound (39.1 g, 100%), $^1$H NMR (CDCl$_3$) δ9.0 (3H, d), 7.5 (10H, m), 5.5 (4H, s).

f. 3,5-dibenzyloxycarbonylaniline 3,5-dibenzyloxycarbonylnitrobenzene (3.91 g, 10 mol) was dissolved in ethyl acetate (50 ml) and tin(II)chloride dihydrate (11.27 g, 50 mmol) was added and the mixture stirred and heated at 70 under an atmosphere of nitrogen for 1 h. The mixture was poured carefully onto 5% sodium hydrogencarbonate solution (200 ml) and a further aliquot of ethyl acetate (100 ml) was added. After shaking, the organic layer was separated and the aqueous layer was extracted with more ethyl acetate (50 ml). The combined organic layers were washed with brine, dried, filtered and evaporated to leave a pale yellow solid (3.25 g, 90%), $^1$H NMR (CDCl$_3$) δ8.1 (1H, d), 7.5 (12H, m), 5.4 (4H, s), 3.8 (2H, br s).

g. N-tert-butyloxycarbonyl-1S-(3,5-dibenzyloxycarbonylphenylaminocarbonyl)-2-(2-fluorophenyl)ethylamine BOC-L-2-fluorophenylalanine (2.61 g, 9.2 mmol) was dissolved in dry dichloromethane (30 ml) and dry diisopropylethylamine (3.2 ml, 18.4 mmol) was added followed by PyBROP (4.3 g, 9.2 mmol). The mixture was stirred at room temperature for 5 min and then 3,5-dibenzyloxycarbonylaniline (2.17 g, 6.0 mmol) was added. The solution was stirred at room temperature overnight and the solution was then washed sequentially with 5% aqueous potassium hydrogensulphate, water, saturated sodium hydrogencarbonate solution and water and finally dried, filtered and evaporated. The crude product was crystallised from ethanol to give the title compound (2.94 g, 0.78%). $^1$H NMR (d$^6$-DMSO) δ10.4 (1H, s), 8.5 (2H, s), 8.2 (1H, s), 7.3 (15H, m), 5.4 (4H, s), 4.3 (1H, m), 2.9 (2H, m), 1.3 (9H,s).

h. 1S-(3,5-dibenzyloxycarbonylphenylaminocarbonyl)-2-(2-fluorophenyl)ethylamine

N-tert-butyloxycarbonyl-1S-(3,5-dibenzyloxycarbonylphenylaminocarbonyl)-2-(2-fluorophenyl)ethylamine (8.0 g, 12.7 mmol) was dissolved in trifluoroacetic acid (40 ml) and stirred at room temperature for 30 min. The solvent was removed by evaporation and the residue taken up in dry dichloromethane (50 ml) and washed with saturated sodium hydrogencarbonate solution (3×30 ml), water (30 ml) and brine (30 ml). The solution was dried over anhydrous sodium sulphate, filtered and evaporated to give the title compound (6.5 g,98%). $^1$H NMR (d$^6$-DMSO) δ8.5 (2H,s), 8.2 (1H,s), 7.3 (14H,m), 5.4 (4H,s), 3.6 (1H,m), 2.9 (1H,m), 2.8 (1H,m).

EXAMPLE 2

(±)-5-(1-(3,5-dicarboxyphenylaminocarbonyl)-2-(2,3,4-trifluorophenyl)ethylaminocarbonyl)-6-(1-cycloheptanemethylaminocarbonyl)benzimidazole The material was prepared essentially as in example 1 except that (±)-BOC-2,3,4-trifluorophenylalanine was used in step g instead of BOC-L-2-fluorophenylalanine. $^1$H NMR (d$^6$-DMSO) δ10.2 (1H, s),8.90 (1H, d), 8.70 (3H, m), 8.4 (1H, s), 8.2 (1H, s ), 7.9 (1H, s), 7.3 (2H, m), 7.2 (2H, s), 4.9 (1H, m), 3.6 (1H, dd), 3.1 (3H, m), 1.6–1.1 (13H, m).

The compound was further characterised and tested as the di-N-methyl-D-glucamine salt. Found: C, 55.49; H, 6.33; N, 9.21. $C_{48}H_{60}F_3N_7O_{17}$ requires C, 53.88 H, 6.22; N, 9.16%.

EXAMPLE 3

5-(1S-(3,5-dicarboxyphenylaminocarbonyl)-2-(3-fluorophenyl)ethylaminocarbonyl)-6-(1-cycloheptanemethylaminocarbonyl)benzimidazole The material was prepared essentially as in example 1 except that BOC-L-3-fluorophenylalanine was used in step g instead of BOC-L-2-fluorophenylalanine. $^1$H NMR (d$^6$-DMSO) δ10.2 (1H, s), 8.9 (1H, s), 8.7 (2H, d), 8.7 (1H, t), 8.4 (1H, s),8.2 (1H, t), 7.8 (1H, br s), 7.4 (1H, m), 7.2 (2H, m), 7.1 (2H, m), 4.8 (1H, m), 3.5 (1H, dd), 3.1 (2H, m), 3.0 (1H, dd), 1.7–1.1 (13H, m).

The compound was further characterised and tested as the di-N-methyl-D-glucamine salt. Found: C, 53.16; H, 6.91; N, 9.18. $C_{48}H_{68}F_3N_7O_{17}$. 2.7H$_2$O requires C, 53.27; H, 6.83; N, 9.06%.

EXAMPLE 4

5-(1S-(3,5-dicarboxyphenylaminocarbonyl)-2-(2-fluorophenyl) ethylaminocarbonyl)-6-(1-adamantanemethylaminocarbonyl)benzimidazole This was prepared essentially as in example 1 except that 1-adamantanemethylamine was used in step c instead of cycloheptanemethylamine. $^1$H NMR (d$^6$-DMSO) δ13.0 (3H, br s), 10.2 (1H, s), 8.9 (1H, d), 8.7 (2H, s), 8.6 (1H, t), 8.4 (1H, s), 8.2 (1H, s), 7.9 (1H, d), 7.4–7.2 (4H, m), 7.1 (1H, s), 4.8 (1H, m), 3.6–2.9 (4H, m), 1.8 (3H, s), 1.6 (6H, m), 1.3 (6H, m).

The compound was further characterised and tested as the di-N-methyl-D-glucamine salt found: C, 55.19; H, 6.77; N, 8.66. $C_{51}H_{70}FN_7O_7$ requires C, 55.10; H, 6.75; N, 8.82%

EXAMPLE 5

5-(1S-(3,5-dicarboxyphenylaminocarbonyl)-2-(3-fluorophenyl)ethylaminocarbonyl)- 6-(1-adamantanemethylaminocarbonyl)benzimidazole This was prepared essentially as in example 4 except that that BOC-L-3-fluorophenylalanine was used in step g instead of BOC-L-2-fluorophenylalanine. $^1$H NMR (d$^6$-DMSO) δ13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (1H, m), 7.2 (4H, m), 4.8 (1H, m), 3.6–2.9 (4H, m), 1.8 (3H, s), 1.7 (6H, q), 1.5 (6H, s).

The compound was further characterised and tested as the di-N-methyl-D-glucamine salt. Found: C, 55.11; H, 6.84; N, 8.90. $C_{51}H_{70}FN_7O_{17}.2H_2O$ requires C, 55.27; H, 6.73; N, 8.85%

EXAMPLE 6

5-(1S-(3,5-dicarboxyphenylaminocarbonyl)-2-(4-fluorophenyl)ethylaminocarbonyl)-6-(1-adamantanemethylaminocarbonyl)benzimidazole This was prepared essentially as in example 4 except that BOC-L-4-fluorophenylalanine was used in step g instead of BOC-L-2-fluorophenylalanine. $^1$H NMR (d$^6$-DMSO) δ13.0 (3H, br s), 10.2 (1H, s), 8.9 (1H, d), 8.7 (2H, s), 8.5 (1H, t), 8.4 (1H, s), 8.2 (1H, s), 7.9 (1H, s), 7.4 (2H, m), 7.2 (3H, m), 4.8 (1H, m), 3.6–2.9 (4H, m), 1.8 (3H, s), 1.7 (6H, q), 1.5 (6H, s).

The compound was further characterised and tested as the di-N-methyl-D-glucamine salt. Found: C, 55.32; H, 6.61; N, 8.74. $C_{51}H_{70}FN_7O_{17}.2H_2O$ requires C, 55.27; H, 6.73; N, 8.85%

EXAMPLE 7

(±)-5-(1-(3,5-dicarboxyphenylaminocarbonyl)-2-pentafluorophenylethylaminocarbonyl)-6-(1-adamantanemethylaminocarbonyl)benzimidazole This was prepared essentially as in example 4 except that (±)-BOC-pentafluorophenylalanine was used in step g instead of BOC-L-2-fluorophenylalanine. $^1$H NMR (d$^6$-DMSO) δ13.0 (2H, br s), 10.2 (1H, s), 8.9 (1H, d), 8.6 (2H, d), 8.5 (1H, t), 8.4 (1H, s), 8.2 (1H, d), 7.9 (1H, s), 7.4 (1H, s), 4.8 (1H, m), 3.5 (1H, dd), 3.2 (1H, dd), 3.0 (2H, d), 1.9 (3H, s), 1.5 (6H, q), 1.4 (6H, s).

The compound was further characterised and tested as the di-N-methyl-D-glucamine salt. Found: C, 50.83; H, 6.04; N, 8.17. $C_{51}H6F_5N_7O_{17}.3.3H_2O$ requires C, 50.87; H. 6.08; N, 8.14%

EXAMPLE 8

(±)-5-(1-(3,5-dicarboxyphenylaminocarbonyl)-2-(2,4-difluorophenyl)ethylaminocarbonyl)-6-(1-adamantanemethylaminocarbonyl)benzimidazole This was prepared essentially as in example 4 except that (±)-BOC-2,4-difluorophenylalanine was used in step g instead of BOC-L-2-fluorophenylalanine. $^1$H NMR (d$^6$-DMSO) δ13.2 (3H, br s), 10.2 (1H, s), 8.9 (1H, d), 8.7 (2H, d), 8.6 (1H, t), 8.4 (1H, s), 8.2 (1H, t), 7.5 (1H, m), 7.3 (2H, m), 7.2 (1H, s), 7.1 (1H, m), 4.8 (1H, m), 3.5 (1H, dd), 3.0 (3H, m), 1.9(3H, s), 1.6 (6H, q), 1.5 (6H, s).

The compound was further characterised and tested as the di-N-methyl-D-glucamine salt. Found: C, 52.83; H, 6.76; N, 8.26. $C_{51}H_{69}F_2N_7O_{17}.4H_2O$ requires C, 52.67; H, 6.68; N, 8.43%

EXAMPLE 9

5-(1S-(3,5-dicarboxyphenylaminocarbonyl)-2-phenylethyl-(N-methylamino)-carbonyl)-6-(1-adamantanemethylaminocarbonyl)benzimidazole This was prepared essentially as in example 4 except that BOC-N-methyl-L-phenylalanine was used in step g instead of BOC-L-2-fluorophenylalanine, $^1$H NMR (d$^6$-DMSO) was consistent with the desired structure as a mixture of tautomers.

The compound was further characterised and tested as the di-N-methyl-D-glucamine salt. Found: C, 55.69; H, 7.04; N, 8.65. C52H73N7O$_{17}$.2H$_2$O requires C, 56.56; H, 7.03; N, 8.88%

EXAMPLE 10

5-(1S-(3,5-ditetrazolylphenylaminocarbonyl)-2-phenylethylaminocarbonyl)-6-(1-adamantanemethylaminocarbonyl)benzimidazole a. Bis pivaloyloxymethyl derivative of 1S-(3,5-ditetrazolylphenylaminocarbonyl)-2-phenylethylamine 5-nitro-isophthalic acid was converted to 5-nitro-3-cyanobenzonitrile via the bis primary amide. Treatment with sodium azide in hot DMF gave the bis tetrazole which was derivatised with POM chloride. Catalytic hydrogenation of the nitro group gave the aniline, which was coupled with BOC-L-phenylalanine using PyBROP then treated with tri-fluoroacetic acid to leave the title compound.

b. Bis pivaloyloxymethyl derivative of 5-(1S-(3,5-ditetrazolylphenylaminocarbonyl)-2-phenylethylaminocarbonyl)-6-(1-adamantanemethylaminocarbonyl)benzimidazole This was prepared essentially as in example 1 steps b and c but using the product of this example step a as substrate in step b instead of 1S-(3,5-dibenzyloxycarbonylphenylaminocarbonyl)-2-(2-fluorophenyl)ethylamine and using 1-adamantanemethylamine in place of cycloheptanemethylamine in step c.

c. 5-(1S-(3,5-ditetrazolylphenylaminocarbonyl)-2-phenylethylaminocarbonyl)-6-(1-adamantanemethylaminocarbonyl)benzimidazole The bis POM derivative prepared in step b (890 mg) was dissolved in saturated methanolic ammonia solution (20 ml) and stirred at room temperature for 5 h. The volatile material was removed by evaporation to leave the title compound (740 mg) as its bis ammonium salt, Found: C, 57.36; H, 6.06; N, 27.17. $C_{37}H_{43}N_{15}O_3$.1.5 H$_2$O requires C, 57.50; H, 5.99; N, 27.18%, $^1$H NMR (d$^6$-DMSO) δ10.2 (1H, s), 8.8 (1H, d), 8.6 (2H, d), 8.4 (2H, m), 7.9 (1H, s), 7.4–7.2 (7H, m), 4.8 (1H, m), 3.5–3.0 (4H, m), 1.8 (3H, s), 1.5 (6H, q), 1.4 (6H, s).

EXAMPLE 11

5-(1S-(3,5-ditetrazolylphenylaminocarbonyl)-2-(2-fluorophenyl)ethylaminocarbonyl)-6-(1-adamantanemethylaminocarbonyl)benzimidazole This was prepared essentially as in example 10 except that BOC-L-2-fluorophenylalanine was used in step a instead of BOC-L-phenylalanine. The compound was isolated and tested as its bis ammonium salt. Found: C, 54.97; H, 5.92; N, 26.06. $C_{37}H_{42}FN_{15}O_3$.2.5 $H_2O$ requires C, 54.94; H, 5.85; N, 25.97%. $^1$H NMR (d$^6$-DMSO) δ10.1 (1H, s), 8.8 (1H, d), 8.4 (5H, m), 7.9 (1H, s), 7.5 (1H, t), 7.4 (1H, t), 7.3 (3H, m), 4.8 (1H, m), 3.6–2.9 (4H, mn), 1.8 (3H, s), 1.5 (6H, q), 1.4 (6H, s).

EXAMPLE 12

5-(1S-(3,5-ditetrazolylphenylaminocarbonyl)-2-(3-fluorophenyl)ethylaminocarbonyl)-6-(1-adamantanemethylaminocarbonyl)benzimidazole This was prepared essentially as in example 10 except that BOC-L-3-fluorophenylalanine was used in step a instead of BOC-L-phenylalanine. The free ditetrazole was obtained on treating the bis ammonium salt with hydrochloric acid. $^1$H NMR (d$^6$-DMSO) δ10.4 (1H, s), 9.5 (1H, s), 9.2 (1H, md, 8.8(3H,m),8.5 (1H, s), 8.0 (1H, s), 7.5 (1H, dd), 7.4 (2H, m), 7.2 (2H, m), 7.1(1H, m),4.9 (1H, m), 3.5 (1H, dd), 3.1 (1H,t),2.9(3H,m),1.8 (3H, s), 1.5 (6H, q), 1.4 (6H, s).

The compound was further characterised and tested as the di-N-methyl-D-glucamine salt. Found: C, 50.34; H, 6.40; N, 17.59. $C_{51}H_{70}FN_{15}O_{13}$.5.0H$_2$O requires C, 50.61; H, 6.66; N, 17.36%

EXAMPLE 13

5-(1S-(3,5-ditetrazolylphenylaminocarbonyl)-2-phenylethylaminocarbonyl)-6-(cycloheptanemethylaminocarbonyl)benzimidazole This was prepared essentially as in example 10 except that cycloheptanemethylamine was used in step c in place of 1-adamantanemethylamine. The free ditetrazole was obtained on treating the bis ammonium salt with hydrochloric acid. $^1$H NMR (d$^6$-DMSO) δ10.4 (1H, s), 8.9 (1H, d), 8.8 (2H, s), 8.7(1H, t),8.5 (1H, s), 8.4 (1H, s), 7.9 (1H, s), 7.4 (4H, m), 7.3 (2H, m), 7.1(1H, m),4.9 (1H, m), 3.5 (1H, dd), 3.0 (2H, t),2.9(1H, dd),1.6–1.0(13H, m).

The compound was further characterised and tested as the di-N-methyl-D-glucamine salt. Found: C, 50.75; H, 6.85; N, 8.42. $C_{48}H_{69}N_{15}O_{13}$.4.0H$_2$O requires C, 50.74; H, 6.83; N, 18.49%,

EXAMPLE 14

5-(1S-(3,5-ditetrazolylphenylaminocarbonyl)-2-(2-fluorophenyl)ethylaminocarbonyl)-6-(cycloheptanemethylaminocarbonyl)benzimidazole This was prepared essentially as in example 13 except that BOC-L-2-fluorophenylalanine was used in step a instead of BOC-L-phenylalanine. The free ditetrazole was obtained on treating the bis ammonium salt with hydrochloric acid. $^1$H NMR (d$^6$-DMSO) δ10.4 (1H, s), 8.9 (1H, d), 8.8 (2H, s), 8.7(1H, t),8.5 (1H, s), 8.4 (1H, s), 7.9 (1H, s), 7.4 (1H, m), 7.3 (1H, m), 7.2(2H, m),7.1(1H, m),4.9 (1H, m), 3.6 (1H, dd), 3.1 (2H, m),2.9(1H, dd),1.6–1.0(13H, m).

The compound was further characterised and tested as the di-N-methyl-D-glucamine salt. Found: C, 50.10; H, 6.74; N, 18.27. $C_{48}H_{68}FN_{15}O_{13}$.4.0H$_2$O requires C, 49.91 H, 6.72; N, 18.19%,

EXAMPLE 15

5-(1S-(3-trifluoroacetylaminosulphonyl-phenylaminocarbonyl)-2-phenylethylaminocarbonyl)-6-(1-adamantanemethylaminocarbonyl)benzimidazole a. 1S-(3-trifluoroacetylaminosulphonylphenylaminocarbonyl)-2-phenylethylamine This was prepared in several steps starting with nitrobenzene-3-sulphonyl chloride. This was converted into the sulphonamide using ammonia in benzene. Trifluoroacetic anhydride was used to introduce the trifluoroacetyl group onto the sulphonamide. Catalytic hydrogenation reduced the nitro group to an amino function and this material was coupled to BOC-L-phenylalananine using the PyBROP method. Removal of the BOC group was achieved with trifluoroacetic acid.

b. 5-(1-adamantanemethylaminocarbonyl)benzimidazole-6-carboxylic acid

A solution of 1-adamantanemethylamine (3.8 g,22mmol) in THF (50 ml) was added to a stirred solution of benzimidazole-5,6-dicarboxylic anhydride (3.8 g,20mmol) and triethylamine (6.1 ml,44 mmol) in THF (250 ml) and the mixture was stirred at room temperature for 1 h. The solvent was partially evaporated to leave approximately ⅔ the original volume which was poured onto 2M hydrochloric acid (400 ml). After standing at 5° C. overnight the resultant white precipitate was filtered and dried to afford the title compound (7.55 g).

c. 5-(1S-(3-trifluoroacetylaminosulphonylphenylaminocarbonyl)-2-phenylethylaminocarbonyl)-6-(1-adamantanemethylaminocarbonyl)benzimidazole The acid described in step b of this example and the amine from step a were coupled using the procedure described in example 1 step c. The crude precipitate was purified by boiling in a 1:1 mixture of dichloromethane and acetone followed by hot filtration. $^1$H NMR (d$^6$-DMSO) δ10.1 (1H, s), 9.0–7.1 (15H, m), 4.8 (1H, m), 3.6–2.7 (4H, m), 1.9 (3H,s ), 1.6 (6H, m), 1.5 (6H, s). Found: C, 55.01; H,5.27; N, 10.33 $C_{37}H_{37}F3N_6O_6S$.3.0H$_2$O requires C, 55.13; H, 5.39; N, 10.43%.

EXAMPLE 16

5-(1S-(3-benzoylaminosulphonylphenylaminocarbonyl)-2-phenylethylaminocarbonyl)-6-(1-adamantanemethylaminocarbonyl)benzimidazole This was prepared essentially as in example 15 except that benzoyl chloride was used in step a instead of trifluoroacetic anhydride.$^1$H NMR (d$^6$-DMSO) δ13.5 (2H, br s), 10.2 (1H, s), 8.8 (1H, d), 8.6 (1H, t), 8.7–7.0 (17H, m), 4.8 (1H, m), 3.5–3.0 (4H, m), 1.9–1.4 (15H, m).

The compound was further characterised and tested as the N-methyl-D-glucamine salt. Found: C, 57.49; H, 6.61; N, 9.72. $C_{49}H_{59}N_7O_{11}S$.3.7H$_2$O requires C, 57.62; H, 6.56; N, 9.60%,

EXAMPLE 17

5-(1S-(3,5-ditetrazolylphenylaminocarbonyl)-2-phenylethylaminocarbonyl)-6-(1-adamantanemethylaminocarbonyl)indole a. 3-Methyl-4-nitrophthalic acid The compound was prepared as in Organic Synthesis Collected Volume 1, 408 from 4-methylphthalic anhydride and fuming nitric acid.

b. Dimethyl 3-methyl-4-nitrophthalate

The compound prepared in step a (4.4 g, 20 mmol) was suspended in methanol (100 ml) and concentrated sulphuric acid (2 ml) and the resulting suspension was heated under reflux for 48 h. After cooling dichloromethane (100 ml) was added and the organic layer was washed with saturated sodium hydrogencarbonate solution. The aqueous layer was re-extracted with dichloromethane (100 ml) and the combined organic layers were washed with washed with brine and dried. The solution was filtered and evaporated to yield a white solid which was purified by recrystallisation from hot methanol. The title compound was isolated as white needles (3.14 g, 62%).

c. Dimethyl 3-(2-N,N-dimethylaminoethylene)-4-nitrophthalate

The dimethyl ester prepared in step c above (3.14 g, 12.4 mmol) was dissolved in DMF (10 ml) and dimethylformamide dimethyl acetal (4.43 g, 37.2 mmol) was added. The reaction mixture was heated at 150° for 6 h and then allowed to cool. The solution was diluted with ethyl acetate (500 ml) and the solution was washed with brine (6×100 ml), dried filtered and evaporated to leave the title compound as a deep red solid (3.70 g, 97%).

d. 5,6-Dimethoxycarbonylindole

The product of step c (1.50 g) was dissolved in toluene (200 ml) and 10% palladium on charcoal(150 mg) was introduced. The reaction was stirred under an atmosphere of hydrogen at room temperature for 1 h. The catalyst was removed by filtration and the solvent by evaporation to leave the title compound (1.14 g).

e. Indole-5,6-dicarboxylic acid

To a stirred solution of the dimethyl ester produced in step d (1.14 g, 4.9 mmol) in a 5:1 mixture of ethanol:water (12 ml) was added solid sodium hydroxide (0.49 g, 12.4 mmol). The solution was stirred at a gentle reflux for 3 h. The solution was acidified on cooling to pH2 with hydrochloric acid and then evaporated. The residue was azeotroped with ethanol and then toluene and dried under vacuum. The residue was then extracted with hot acetone (5×20 ml) and the combined extracts were evaporated to leave the title compound (870 mg).

f. Indole-5,6-dicarboxylic acid anhydride

The product of step e (870 mg) was heated strongly with a heat gun for 10 minutes under vacuum. This left the title compound (800 mg)

g. 5-(1S-(3,5-ditetrazolylphenylaminocarbonyl)-2-phenylethylaminocarbonyl)-6-(1-adamantanemethylaminocarbonyl)indole This was prepared essentially as in example 10 except that indole-5,6-dicarboxylic acid anhydride was used in step b instead of benzimidazole-5,6-dicarboxylic acid anhydride.

A mixture of regioisomers was obtained which was separated by column chromatography (silica 75% dichloromethane 25% ethyl acetate) immediately prior to final deprotection The less polar regioisomer was converted to the compound of this example. $^1$H NMR (d$^6$-DMSO) δ11.5 (1H, s), 10.4 (1H, s), 8.8 (3H, m), 8.5 (2H, m), 7.7 (1H, s), 7.5 (1H, t), 7.4–7.0 (6H, m), 6.5 (1H, s), 4.8 (1H, m), 3.5–2.9 (4H, m), 1.8 (3H, s), 1.5 (6H, q), 1.3 (6H, s).

The compound was further characterised and tested as the N-methyl-D-glucamine salt. Found: C, 53.94; H. 6.91; N, 16.73. $C_{52}H_{72}N_{14}O_{13}.3H_2O$ requires C, 54.06; H, 6.80; N, 16.97%

EXAMPLE 18

6-(1S-(3,5-ditetrazolylphenylaminocarbonyl)-2-phenylethylaminocarbonyl)-5-(1-adamantanemethylaminocarbonyl)indole This was prepared essentially as in example 17 except that the more polar regioisomer isolated when regioisomers were separated was converted to the title compound. $^1$H NMR (d$^6$-DMSO) δ11.5 (1H, s), 10.4 (1H, s), 8.8 (3H, m), 8.5 (2H, m), 7.9 (1H, s), 7.5 (1H, t), 7.4–7.0 (6H, m), 6.6 (1H, s), 4.8 (1H, m), 3.6–2.9 (4H, m), 1.8 (3H, s), 1.5 (6H, q), 1.3 (6H, s).

The compound was further characterised and tested as the N-methyl-D-glucamine salt. Found: C, 54.21; H, 6.62; N, 16.81. $C_{52}H_{72}N_{14}O_{13}.3H_2O$ requires C, 54.06; H, 6.80; N, 16.97%

EXAMPLE 19

5-(1R-(3,5-dicarboxyphenylaminocarbonyl)-2-(2-fluorophenyl)ethylaminocarbonyl)-6-(1-adamantanemethylaminocarbonyl)-benzimidazole The material is prepared essentially as in example 1 except hat BOC-D-2-fluorophenylalanine is used in step g instead of BOC-L-2-fluorophenylalanine. $^1$H NMR (d$^6$-DMSO) δ13.0 (3H, br s), 10.2 (1H, br s), 8.9 (1H, d), 8.74 (2H, s), 8.7 (1H, t), 8.4 (1H, s), 8.2 (1H, s), 7.8 (1H, s), 7.5–7.1 (5H, m), 4.8 (1H, m), 3.5 (1H, m), 3.3–3.1 (3H, m), 1.6–1.1 (13H, m).

EXAMPLE 20

(COMPARATIVE)

5-(1S-(3,5-dicarboxyphenylaminocarbonyl)-2-phenylethylaminocarbonyl)-6-(1-adamantylmethylaminocarbonyl)indole.

A solution of indole-5,6-dicarboxylic anhydride (1.87 g,10 mmol) and 1S-(3,5-dibenzyloxycarbonylphenylaminocarbonyl)-2-phenylethylamine (4.96 g,9.8 mmol) in dry acetonitrile (100 ml) was heated under reflux for 30 min. The mixture was cooled and stood at room temperature overnight. The resultant white precipitate was filtered and dried to give 5-(1S-(3,5-dibenzyloxycarbonylphenylaminocarbonyl)-2-phenylethylaminocarbonyl)-6-(1-adamantylmethylaminocarbonyl)-indole (3.25 g). This was hydrogenolysed, following the procedure used in example 1 step d, to give the title compound. $^1$H NMR (d$^6$-DMSO) δ11.5 (1H, s), 10.2 (1H, s), 8.7 (1H, d), 8.6 (2H, s), 8.4 (1H, t), 8.2 (1H, s), 7.7 (1H, s), 7.5 (1H, s), 7.2 (6H, m), 6.5 (1H, s), 4.8 (1H, m), 3.5 (1H, m), 3.0 (3H, m), 1.8 (3H, s), 1.5 (6H, m), 1.4 (6H, s).

The compound was further characterised and tested as the di-N-methyl-D-glucamine salt. Found : C, 58.05; H, 6.99; N, 7.88. $C_{52}H_{72}N_6O_{17} \cdot H_2O$ requires C, 58.31; H, 6.96; N, 7.85%.

EXAMPLE 21

5-(1S-(3,5-dipivaloyloxycarbonylmethyloxycarbonyl-phenylaminocarbonyl)-2-(2-fluorophenyl) ethylaminocarbonyl)-6-(cycloheptanemethylaminocarbonyl) benzimidazole The product of example 1 was converted to its disodium salt using 2 equivalents of sodium hydrogen carbonate. The salt (687 mg, 1 mmol) was suspended in dry DMF (10 ml) and chloromethylpivalate (288 µl, 2 mmol) was added. The mixture was heated at 100° C. for 1 h and mostly went into solution. After cooling, the solution was added to 2M hydrochloric acid (50 ml) and extracted with dichloromethane. The organic layer was washed with brine (2×25 ml), dried (magnesium sulphate), filtered and evaporated to leave an oil which was purified by column chromatography (silica, 95% dichloromethane 5% methanol) to leave the title compound (157 mg) as a white solid. $^1$H NMR (d$^6$-DMSO) δ13.0 (1H, br s), 10.2 (1H, br s), 8.9 (3H, m), 8.6 (1H, t), 8.4 (1H, s), 8.2 (1H, s), 7.8 (1H, m), 7.4–7.2 (5H, m), 6.0 (4H, s), 4.8 (1H, m), 3.5 (1H, m), 3.3–3.1 (3H, m), 1.6–1.1 (13H, m).

The compounds of the examples were tested using the following in vivo assays:

1. Ghosh and Schild anaesthetised rat preparation (intravenous drug administration)

Rats were fasted overnight with free access to water. They were anaesthetised with 1.8 ml/kg urethane 20% w.v. i.p. A midline incision was made in the abdomen and the pyloric sphincter and the cardiac sphincters were cannulated using small plastic tubing. The jugular veins were cannulated and tracheotomy was also carried out. The rats were placed on a temperature regulated mat (37°–39° C.) to maintain body temperature and the stomachs were perfused at 1 ml/min with a glucose-containing electrolyte solution. The pH of the perfusate exiting the stomach was measured continuously. The rats were allowed to stabilise for approximately 15–20 min. leading to a satisfactory baseline pH. Pentagastrin infusion (sub-maximal acid secretory dose 0.1 µg/kg/min) was administered via a jugular vein. Pentagastrin induced acid secretion took approximately 5 min. to begin and usually stabilised within 30 min. A bolus dose of the test compound was administered via the contralateral jugular vein and the pH response monitored for 60 min. Responses were measured as the peak percentage with respect to the change in pH evoked by pentagastrin infusion over the baseline. The results obtained are set out in Table 1.

TABLE 1

| Example No. | i.v. dose µmol/kg | % i.v. inhibition |
| --- | --- | --- |
| 1 | 0.1 | 55 |
| 2 | 0.025 | 38 |
| 3 | 0.025 | 37 |

TABLE 1-continued

| Example No. | i.v. dose µmol/kg | % i.v. inhibition |
| --- | --- | --- |
| 4 | 0.1 | 62 |
| 5 | 0.025 | 60 |
| 6 | 0.025 | 66 |
| 7 | 0.025 | 47 |
| 8 | 0.025 | 38 |
| 9 | 0.1 | 39 |
| 10 | 0.025 | 81 |
| 11 | 0.025 | 58 |
| 12 | 0.025 | 63 |
| 13 | 0.025 | 28 |
| 14 | 0.025 | 35 |
| 15 | 0.025 | 44 |
| 16 | 0.025 | 47 |
| 17 | 0.025 | 62 |

2. Conscious, chronic gastric fistula beagle dogs (intragastric drug administration)

Dogs with chronic in-dwelling gastric fistula were fasted overnight with free access to water. They were placed on a table and lightly restrained. The gastric fistula was opened, cleared of food debris and flushed with up to 30 ml of tepid water. Thereafter the gastric contents were collected under gravity every 15 min. and the total titratable acidity ws determined against 0.01M NaOH. After a 30 min settling period 50 ml of water or a solution of the test compound was instilled into the stomach via the gastric fistula and the fistula sealed for 45 min. After 45 min. the fistula was opened, any stomach contents collected and titrated as before. A single sub-maximal, subcutaneous injection of pentagastrin (4–8µg/kg) was administered into the scruff and the subsequent gastric secretions were collected over the following 75 min at 15 min intervals. The acid secreted over the test 75 min period was aggregated and compared with the typical response of each individual dog to pentagastrin challenge in the absence of drug as assessed from the mean of the last 6 control studies. Results are set out in Table 2, expressed as the percentage inhibition.

TABLE 2

| Example No. | i.g. dose µmol/kg | % i.g. inhibition |
| --- | --- | --- |
| 1 | 5 | 47 |
| 2 | 10 | 27 |
| 3 | 10 | 35 |
| 4 | 5 | 50 |
| 5 | 10 | 58 |
| 6 | 10 | 45 |
| 7 | 2.5 | 22 |
| 8 | 2.5 | 35 |
| 9 | 10 | 49 |
| 10 | 10 | 48 |
| 11 | 5 | 41 |
| 12 | 10 | 44 |
| 13 | 2.5 | 43 |
| 14 | 25 | 39 |
| 15 | 10 | 21 |
| 16 | 10 | 45 |
| 17 | 10 | 59 |
| 18 | 5 | 24 |
| 20* | 40 | i.a. |

*(comparative)
i.a. = inactive as tested

3. Conscious, chronic gastric fistula beagle dogs (intravenous drug administration)

Animals were prepared as above and an intravenous cannula with a two-way tap was placed in the foreleg vein for continuous infusion of initially saline and subsequently pentagastrin to evoke a background, sub-maximal acid secretory response. 1 hour after commencing the pentagastrin infusion a bolus dose of the test compound was administered and the response monitored for at least 1 further hour. Responses were measured as the peak percentage reduction in acid secretion with respect to the pre-dose 15 min sample. Results are set out in Table 3.

TABLE 3

| Example No. | i.v. dose μmol/kg | % i.v. inhibition |
| --- | --- | --- |
| 1 | 0.025 | 48 |
| 4 | 0.05 | 76 |
| 5 | 0.025 | 87 |
| 10 | 0.0067 | 56 |
| 11 | 0.0067 | 83 |

We claim:

1. A compound of the formula

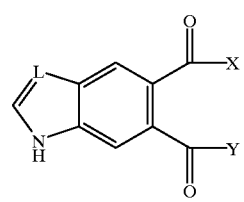

wherein

L is N or C, one of X and Y is —NH—CH$_2$—R$^2$ (wherein R$^2$ is cycloheptyl or 1-adamantyl) and the other is

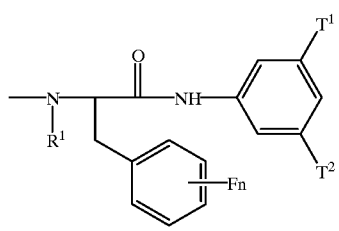

in which R$^1$ is H or methyl,

T$_1$ and T$^2$ are independently H or Z(CH$_2$)$_m$—, wherein m is from 0 to 3 and Z is a carboxy group, a tetrazolyl group, CF$_3$CONHSO$_2$—, PhCONHSO$_2$—, isopropyl-OC(O)NHSO$_2$— or a group selected from

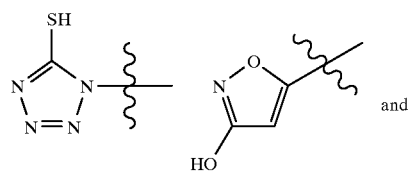 and 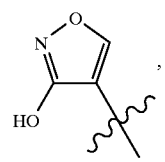

(provided that T$^1$ and T$^2$ are not both H and that T$^1$ and T$^2$ are not both carboxy when L is C); and n is from 0 to 5 or a pharmaceutically acceptable salt or prodrug thereof.

2. A compound according to claim 1, wherein L is N.

3. A compound according to claim 1 wherein n>0.

4. A compound according to claim 2 wherein n=0 and T$^1$ and T$^2$ are other than carboxy.

5. A compound according to claim 1 wherein m=0.

6. A pharmaceutical composition comprising a compound according to claim 1 in admixture with a pharmaceutically acceptable excipient or carrier.

7. A composition according to claim 6, wherein said excipient or carrier is suitable for oral administration.

8. A method of treating disorders for which a lowered gastrin or cholecystokinin level has a therapeutic effect, comprising administering to a mammal in need thereof an effective gastrin-inhibiting or cholecystokinin-inhibiting amount of a compound according to claim 1.

9. A method of preparing a compound according to claim 1, said method comprising the steps of a) reacting a compound of the formula

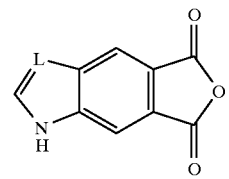

with a compound of the formula H$_2$N—CH$_2$—R$^2$ wherein L and R$^2$ are as defined in claim 1, b) reacting the product with a compound of the formula

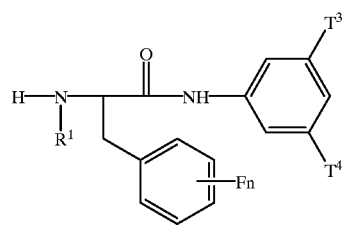

wherein R$^1$ and n are as defined in claim 1, and T$^3$ and T$^4$ are independently H or Z' (CH$_2$)$_m$— (wherein m is from 0 to 3 and Z' is a protected carboxy group, a protected tetrazolyl group, CF$_3$CONHSO$_2$—, PhCONHSO$_2$— or a suitable precursor group and c) deprotecting and/or functionalising $T^3$ and/or $T_4$ if required.

10. The method according to claim 9, wherein Z' is a precursor group selected from the group consisting of HO— and $H_2N$—.

11. A method of preparing a compound according to claim 1, said method comprising the steps of a) reacting a compound of the formula

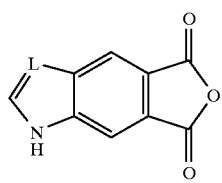

with a compound of the formula

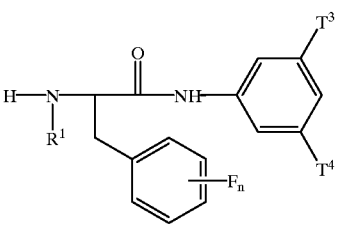

wherein $R^1$, L and n are as defined in claim 1, and $T^3$ and $T^4$ are other than carboxyl, b) reacting the product with a compound of the formula $H_2N$—$CH_2$—$R^2$ wherein $R^2$ is as defined in claim 1, and c) deprotecting and/or functionalising $T^3$ and/or $T^4$ if required.

* * * * *